US009012604B2

(12) United States Patent
Jeong et al.

(10) Patent No.: US 9,012,604 B2
(45) Date of Patent: Apr. 21, 2015

(54) TRIAZANONANE DERIVATIVES OR PHARMACEUTICALLY ACCEPTABLE SALT THEREOF FOR ENHANCED FLUORINE-18 LABELING

(75) Inventors: Jae Min Jeong, Seoul (KR); Dinesh Shetty, Seoul (KR); Dong Soo Lee, Seoul (KR); June-Key Chung, Seoul (KR); Myung Chul Lee, Seoul (KR)

(73) Assignee: Snur & DB Foundation, Seoul (KR)

( * ) Notice: Subject to any disclaimer, the term of this patent is extended or adjusted under 35 U.S.C. 154(b) by 0 days.

(21) Appl. No.: 13/983,053

(22) PCT Filed: Feb. 1, 2012

(86) PCT No.: PCT/KR2012/000790
§ 371 (c)(1),
(2), (4) Date: Jul. 31, 2013

(87) PCT Pub. No.: WO2012/105814
PCT Pub. Date: Aug. 9, 2012

(65) Prior Publication Data
US 2013/0317196 A1    Nov. 28, 2013

(30) Foreign Application Priority Data

Feb. 1, 2011    (KR) .................. 10-2011-0010202

(51) Int. Cl.
| | | |
|---|---|---|
| *A61K 38/12* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07D 255/02* | (2006.01) | |
| *A61K 51/04* | (2006.01) | |
| *C07K 7/64* | (2006.01) | |

(52) U.S. Cl.
CPC ............ *C07D 255/02* (2013.01); *A61K 51/044* (2013.01); *C07K 7/64* (2013.01)

(58) Field of Classification Search
None
See application file for complete search history.

(56) References Cited

U.S. PATENT DOCUMENTS

| | | |
|---|---|---|
| 2005/0120494 A1 | 6/2005 | Vidal |
| 2008/0253964 A1 | 10/2008 | McBride |
| 2009/0155166 A1 | 6/2009 | McBride |
| 2009/0246130 A1 | 10/2009 | McBride |

FOREIGN PATENT DOCUMENTS

| | | |
|---|---|---|
| WO | 2008/088648 | 9/2008 |
| WO | 2009/079024 | 6/2009 |

OTHER PUBLICATIONS

Liu et al. Bioconjug. Chem. (2009) 20: 2199-2213.
McBride et al. J. Nucl. Med (2009) 50: 991-998.
Laverman et al. J. Nucl. Med (2010) 51: 454-461.
McBride et al. Bioconjug. Chem. (2010) 21: 1331-1340.
Shetty et al. Chem. Comm. (2011) 47: 9732-9734.
International Search Report, dated Sep. 15, 2012 for related application No. PCT/KR2012000790.

*Primary Examiner* — Marcela M Cordero Garcia
*Assistant Examiner* — Kaipeen Yang
(74) *Attorney, Agent, or Firm* — Cheryl H. Agris; Agris & von Natzmer, LLP (57) ABSTRACT

The present invention relates to a triazanonane derivative indicated by the chemical formula 1 below, or a pharmaceutically acceptable salt thereof, and a method for preparing same, and the triazanonane derivative according to the present invention forms a complex with a metal-fluoride and displays an effect of increasing the labeling efficiency up to 78-90% when labeling F-18, thus enabling use in various radioactive medicine labeling

[Chemical Formula 1]

(In the chemical formula 1, $R^1$, $R^2$, A. E. X, n and m are as defined in the present description.)

11 Claims, 3 Drawing Sheets

TRIAZANONANE DERIVATIVES OR PHARMACEUTICALLY ACCEPTABLE SALT THEREOF FOR ENHANCED FLUORINE-18 LABELING

CROSS-REFERENCE TO RELATED APPLICATIONS

This patent application is a U.S. national phase under 35 U.S.C. 371 of PCT/KR2012/000790 filed on Feb. 1, 2012, which claims the benefit of priority from Korean Patent Applications No. 10-2011-0010202, filed on Feb. 1, 2011, in the Korean Intellectual Property Office, the disclosure of which is incorporated herein by reference in its entirety.

TECHNICAL FIELD

The present invention relates to triazanonane derivatives or pharmaceutically acceptable salt thereof for enhanced fluorine-18 labeling.

BACKGROUND ART

Fluorine-18 (F-18), which is the most widely used positron emission tomography (PET) substance, is generally obtained from cyclotron and supplied in dissolved form, i.e., supplied as fluoride which does not bear chemical activity. Accordingly, in aqueous solution, F-18 can hardly label biologically active substance. Therefore, the general process involves removal of water, addition of tetrabutyl ammonium or crown ether, and reaction with precursor with good leaving group and organic solvent, which enables F-18 activation and labeling.

In order to remove water to prepare positron-emitting radiopharmaceutical product with F-18 labeling, generally, heating to bubble the gas, or evaporating in reduced pressure, are used. However, there are shortcomings. That is, the necessity for 1 to 10 mL or larger container hinders space-efficiency of the automatic synthesizing equipment, and time consumption for water evaporation that is longer than the other processes is another shortcoming. Accordingly, many have studied on methods for labeling F-18 which does not require water removal process.

Certain frontier suggestion was made by Immunomedics, Inc., as disclosed on WO 2008/088648, US 2008/0253964, US 2009/0155166 and a series of non-patent documents including: McBride W J, et al., "A novel method of 18F radiolabeling for PET" (J Nucl Med (2009) 50:991-998); Layerman P, et al., "A novel facile method of labeling octreotide with 18F-fluorine" (J Nucl Med (2010) 51:454-461); and McBride W J, et al., "Improved 18F labeling of peptides with a fluoride-aluminum-chelate" (Bioconjug Chem (2010) 21:1331-1340)). According to the above method, complex of F-18 and aluminum is first formed, and then chelate is formed on NOTA derivative attached to bioactive substance such as octreotide. Because the reaction occurs in aqueous solution, water removal process can be omitted, thus providing advantage such as simpler reaction process and faster rate.

However, although the F-18 labeling method proposed by Immunomedics Inc. provides more economic ways to label F-18 thanks to omission of water removal process, the labeling efficiency is limited to around 50% and this has to be actively improved.

While studying ways to improve labeling efficiency, the present inventors were able to synthesize novel triazanonane derivatives and confirm that the triazanonane derivatives provide effect of improved F-18 labeling efficiency, and therefore, completed the present invention.

Objects

It is an object of the present invention to provide triazanonane derivatives or pharmaceutically acceptable salt thereof.

It is another object of the present invention to provide complex of the triazanonane derivatives and metal and fluorine.

It is yet another object of the present invention to provide a radiopharmaceutical product comprising a complex of the triazanonane derivatives and metal and fluorine.

It is yet another object of the present invention to provide a kit to form complex of the triazanonane derivatives and aluminum and fluorine-18.

SUMMARY OF DISCLOSURE

In order to achieve the objects mentioned above, the present invention provides triazanonane derivatives expressed by Formula 1 or pharmaceutically-acceptable salt thereof:

[Chemical Formula 1]

(wherein the substituent is as defined herein.)

Further, the present invention provides a complex of the triazanonane derivatives and metal and fluorine.

Further, the present invention provides a radiopharmaceutical product comprising a complex of the triazanonane derivatives and metal and fluorine.

Further, the present invention provides a kit to form a complex of the triazanonane derivatives and aluminum and fluorine-18.

Advantageous Effects

The triazananone derivatives or pharmaceutically acceptable salt thereof according to the present invention can be widely used for a variety of radioactive pharmaceutical labeling, since it stably forms complex with metal and F-18 in octahedral structure which enables 78~90% F-18 labeling.

DETAILED DESCRIPTION OF DISCLOSURE

Hereinafter, the present invention will be explained in greater detail.

The present invention provides triazanonane derivatives expressed by Chemical Formula 1 or pharmaceutically acceptable salt thereof:

[Chemical Formula 1]

where $R^1$ and $R^2$ are independently OH, SH, NH$_2$ or C$_1$~C$_{10}$ alkoxy;
A is CH$_2$, C(=S) or C(=O);
E is CH$_2$, C(=S), C(=O) or phenyl;
X is atom group with biological activity or linker activated or activatable to bond to another molecule;
N is integer between 0 and 10, which may be an integer between 3 and 10 when E is not phenyl; and
m is integer between 0 and 5.

In one preferred embodiment,
each of $R^1$ and $R^2$ is independently OH or t-butoxy;
A is CH$_2$ or C(O);
E is CH$_2$, C(=O) or phenyl;
X is atom group selected from amino acid, peptide, protein, nucleic acid, vitamin, hormone, neurotransmitter, sugar, nanoparticle, microparticle, fat, fatty acid, nitroimidazole or derivatives thereof;
N is integer between 0 and 10, or between 3 and 10 when E is not phenyl; and
m is integer between 0 and 3.

According to one embodiment, the triazanonane derivatives of Chemical Formula 1 have a mother nucleus ('NO2A') composed of triazanonane ring with two nitrogen atoms incorporated with acetyl group, and the other one nitrogen atom containing various biological active substances.

O, N, S atoms, which can give electron to metal, are preferably located away from the center of NO2A to avoid a situation where the O, N, S atoms form pentagon or hexagon with the metal intended for chelation at the center of the NO2A, to thus prevent deterioration of the labeling efficiency due to hindered formation of the F-18 and metal complex.

Accordingly, possible hindrance to F-18 labeling is prevented, in which the NO2A mother nucleus misses N, O or S as substituent or in which these atoms form heptagon or higher polygon when forming complex with metal.

When X is atom group with bioactivity, X may be amino acid, peptide, protein, nucleic acid, vitamin, hormone, neurotransmitter, sugar, nanoparticle, microparticle, fat, fatty acid and derivatives thereof.

The peptide is the most actively researched substance for the fluorine-18 labeling substance, and includes octreotide derivatives, bombesin, vasoactive intestinal peptide (VIP), cholecystokinin, neurotensin, EGF, VEGF, RGD, CXCR4 ligand, substance P, matrix metalloproteinase (MMP), lycin glutamate urea, or cysteine glutamate urea.

The protein includes human serum protein, glucoprotein, lipid protein or neoglycoprotein, antibody, Proantibody, antibody fragment, or engineered antibody.

The nucleic acid includes DNA (mtDNA, cDNA), RNA (tRNA, mRNA, siRNA, microRNA, rRNA, ncRNA, sgRNA, shRNA, snRNA, miRNA, snoRNA, LNA), or aptamer.

When X is activated, or activatable linker or bondable linker, X may be carboxyl, hydroxyl, amine, halogen, N-hydroxysuccinimide ester, tetrafluorophenol ester, pentafluorophenol ester, maleimide, haloacetate, hydrazine, hydroxylamine, sulfhydryl, thioester, desulfide, aldehyde, isothiocyanate azide or acetylene.

This is to utilize the fact that the triazanonane derivatives of Chemical Formula 1 easily bond to the biological active substances when attached with proper linker and activated. Table 1 below lists various linkers and reactants thereof.

TABLE 1

| No. | Reactant | Product (linker) |
|---|---|---|
| 1 | —COOH + H$_2$N— | —CONH— |
| 2 | —X + H$_2$N— | —$\overset{H}{\underset{}{N}}$— |
| 3 | —X + HS— | —S— |
| 4 | ![structure] N-hydroxysuccinimide ester + H$_2$N— | —C(=O)—NH— |
| 5 | tetrafluorophenol ester + H$_2$N— | —C(=O)—NH— |
| 6 | pentafluorophenol ester + H$_2$N— | —C(=O)—NH— |

TABLE 1-continued

| No. | Reactant | Product (linker) |
|---|---|---|
| 7 | maleimide (—N(C=O)CH=CH(C=O)—) + HS— | —N(C=O)CH(S—)CH2(C=O)— (thioether-succinimide) |
| 8 | —C(=O)—CH2—I + HS— | —C(=O)—CH2—S— |
| 9 | —NHNH2 + HC(=O)— | —NHN=CH— |
| 10 | —ONH2 + HC(=O)— | —ON=CH— |
| 11 | —S—S— | HS— |
| 12 | —C(=O)—S— | HS— |
| 13 | —N=C=S + H2N— | —NH—C(=S)—NH— |
| 14 | —N3 + HC≡C— | triazole ring (—N—N=N— with C) |

Referring to Table 1, first, the amino group at #1 is the example of linker that can bond to carboxyl group. The amino group can be associated by forming amide bond with carbodiamide, or by activating with halogen (#2) or sulfonate (#3) for reaction with amino group or sulfhydryl group. Further, the most typical example of activated linker can be N-hydroxysuccinicamide (NHS) ester (#4). The NHS ester reacts with amino group, acting as a leaving group to result in amide coupling as the two substances are coupled. The similar linker is tetrafluoro phenol (#5) or pentafluoro phenol (#6). Maleiamide (#7) or iodoacetate (#8) can also be contained and easily bond to molecule with sulfhydryl group. The disulfide (#11) is usable as the linker as this is reduced to thus facilitate exposure of sulfhydryl group, and thioester (#12) can also be sulfhydryl group when hydrolyzed. The molecule with hydrazine (#9) or hydroxylamine (#10) residue bonds to aldehyde, and isothiocyanate (#13) bonds to amine group to form isourea coupling, so is usable as a linker, and wide and acetylene (#14) with click reaction can bind with very high efficiency, so are usable as a linker.

The triazanonane derivatives expressed by Chemical Formula 1 according to an embodiment may preferably include:
1) 4,7-bis(carboxymethyl)-1,4,7-triazonane-1-butyric acid;
2) 4,7-bis(carboxymethyl)-1,4,7-triazonane-1-pentanoic acid;
3) 1-(1-amino-butyl)-4,7-bis(carboxymethyl)-1,4,7-triazanonane;
4) cRGDyK-1,4,7-triazacyclononane-1,4-diacetate-7-butylamide;
5) 4,7-bis(carboxymethyl)-1-(4-aminobenzyl)-1,4,7-triazanonane; and
6) 4,7-bis(carboxymethyl)-1-(4-isothiocyanatobenzyl)-1,4,7-triazanonane.

The triazanonane derivatives expressed by Chemical Formula 1 according to the present invention may be used in the form of a pharmaceutically acceptable salt, and acid addition salt, formed by pharmaceutically acceptable free acid, is useful as the salt. The 'pharmaceutically acceptable salt' as used herein refers to a certain organic or inorganic addition salt of the base compound of Chemical Formula 1 which is at such a concentration that it is relatively non-toxic to a patient and has harmless effective action, and adverse side effect from the salt does not counteract against the benefit of the base compound of Chemical Formula 1. The salt may use inorganic and organic acids as the free acid, in which the inorganic acid may include hydrochloric acid, hydrobromic acid, nitric acid, sulfuric acid, perchloric acid, phosphoric acid and the like, and the organic acid may include citric acid, acetic acid, lactic acid, maleic acid, Fumaric acid, gluconic acid, methane sulfonic acid, glycol acid, succinic acid, tartaric acid, galactronic acid, embonic acid, glutamic acid, aspartic acid, oxalic acid, (D) or (L) malic acid, maleic acid, methane sulfonic acid scaly, ethane sulfonic acid, 4-toluene sulfonic acid, salicylic acid, citric acid, benzoic acid, etc. Furthermore, these salts may include alkali metal salt (e.g., sodium salt, potassium salt, etc.) and alkaline earth metal salts (e.g., calcium salt, magnesium salt, etc.), and so on. For example, acid addition salt may include acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydro-bromide/bromide, hydroiodide/iodide, isethionate, lactate, malate, maleate, malonate, mesylate, methyl sulfate, naphthyl acrylate, 2-naphsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethyl amine, diolamine, glycine, lysine, magnesium, meglumine, olamine, potassium, sodium, tromethamine, zinc salts, and among the above, hydrochloride or trifluoroacetate is preferred.

Further, the triazanonane derivatives expressed by Chemical Formula 1 according to the present invention may include not only pharmaceutically acceptable salt, but also all the salts, isomers, hydrates or solvates.

The addition salt may be prepared in a conventional manner, such as, for example, by dissolving the compound of Chemical Formula 1 in water-miscible organic solvent such as, for example, acetone, methanol, ethanol, or acetonitrile, and adding an excess of organic acid or aqueous solution of inorganic acid, to yield precipitation or crystallization, allowing solvent or the excess of acid to evaporate from the mixture, and then drying the same to give addition salt or suction-filtering the precipitate salt.

According to the present invention, a method for preparing triazanonane derivatives of Chemical Formula 1 is provided, which may include the steps of:

preparing a compound of Chemical Formula 7 by allowing NO2A derivatives represented by Formula 5 to react with alkyl bromide of Chemical Formula 6 in organic solvent and base (step 1); and preparing a compound of Chemical Formula 3 by hydrolyzing the compound of Chemical Formula 7 obtained at step 1 in organic solvent (step 2), as is expressed by:

[Reaction Formula 1]

where $R^1$, $R^2$, E, X, n and m are as defined by Formula 1, and R is methyl or ethyl.

The preparation method according to an embodiment will be explained in greater detail below by steps.

Step 1

At step 1, NO2A derivative of Chemical Formula 5 and alkyl bromide of Chemical Formula 6 as the starting materials are allowed to react in organic solvent and base, to yield the compound of Chemical Formula 7. To be specific, the organic solvent may use one selected from the group consisting of acetonitrile tetrahydrofuran, methylene chloride, dimethylformamide and dimethylsulfoxide or mixture solvent thereof, among which acetonitrile and tetrahydrofuran are preferably used.

The base may preferably be potassium carbonate or sodium carbonate, although potassium carbonate is preferably used.

In one embodiment, NO2A derivatives of Chemical Formula 5 and alkyl bromide of Chemical Formula 6, and potassium carbonate are put into a reaction vessel, followed by acetonitrile or tetrahydrofuran. After stirring for 20 hr at room temperature, the compound of Chemical Formula 7 is obtained by column chromatography.

Step 2

At step 2, the compound of Chemical Formula 7 prepared at step 1 is hydrolyzed in organic solvent to give the compound of Chemical Formula 3. To be specific, ethanol or 1,4-dioxane may be used as the organic solvent.

In one embodiment, the compound of Chemical Formula 7 is added with lithium hydroxide in ethanol solvent, and after stirring at 50° C. for 24 hr, or with the use of concentrated hydrochloric acid in the presence of 1,4-dioxane and stirring at room temperature for 12 hr, the compound of Chemical Formula 3 is obtained by RP-HPLC.

Figure 3:
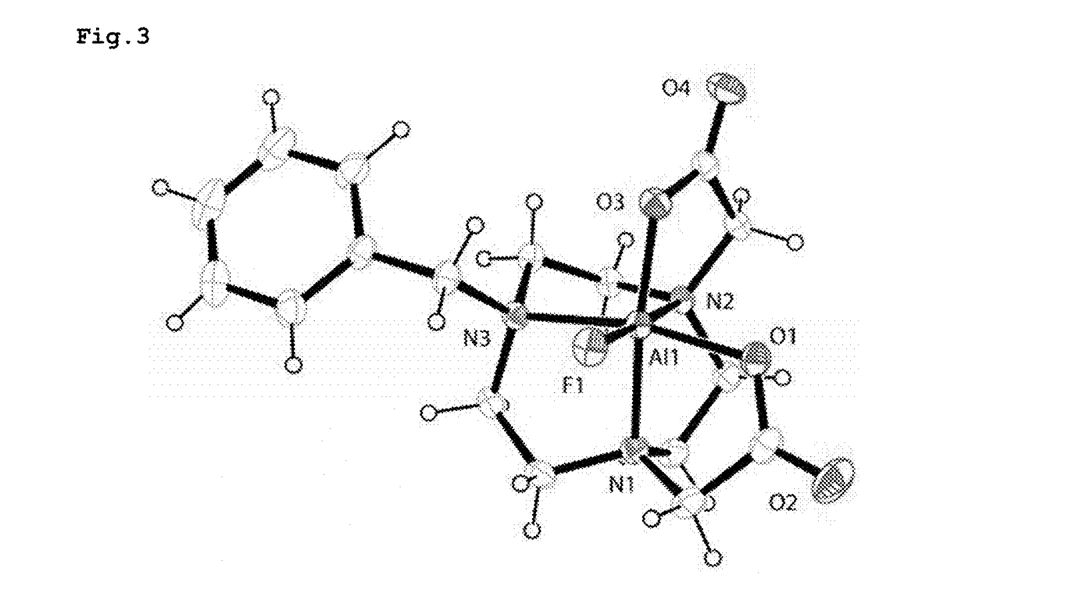
FIG. 3 is a three-dimensional diagram of chemical structure by X-ray crystallography of a stable complex of the derivatives of the compound of Chemical Formula 1 with aluminum fluoride, according to an embodiment of the present invention.

Furthermore, according to the present invention, the complex is provided, in which the triazanonane derivative, which is the compound of Chemical Formula 1 removed of protective group, form with metal and fluorine an octahedral structure with six ligands (see FIG. 3). The metal may preferably be aluminum, gallium, indium, thallium, yttrium or ruthenium.

When aluminum, among other metals, bonds to the center of the triazanonane ring of the compound of Chemical Formula 1, the ligands of the three N atoms and $R^1$ and $R^2$ readily bond to aluminum, and thus form a stable, pentagon structure with aluminum binding. Since aluminum bonds to six ligands, one more bond is possible. Bonding to F-18, which is added to the compound for the purpose of labeling, will be hindered, if the remaining ligand in the molecular structure bonds. In other words, F-18 bonding will be facilitated, if bonding to the remaining ligand in the molecular structure is unstable.

Accordingly, when n is 1 or 2, and E is $CH_2$ or C=O in the compound of Chemical Formula 1, and when X is the ligand such as OH that can give electron pair, the aluminum forming complex and X bond together to form stable pentagon or hexagon structure. When the stable structure forms, this hinders bonding between F-18 and aluminum for labeling, which deteriorates labeling efficiency in turn.

On the contrary, when n is 3 or above, and when E is $CH_2$ or C=O, and when X is the ligand that can give electron pair, the aluminum forming complex and X bond together to form an unstable, heptagonal or higher ring structure. As a result, the formation of unstable structure facilitates bonding between F-18 and aluminum for labeling, and thus increases labeling efficiency.

Further, when E is phenyl ring, since complex containing the same is hardly possible, this will facilitate bonding of F-18 and aluminum and provide increased F-18 labeling efficiency.

According to the method of preparing the complex explained above, $^{18}F$ labeling may use polymer cartridge. That is, 2 mM of $MCl_3$ stock liquid of $MCl_3.6H_2O$ (M is metal) dissolved in 0.1M of sodium acetate buffer solution (pH 4), is activated by flowing 0.4 M $KHCO_3$ and distilled water to polymer cartridge, i.e., to QMA light cartridge, and $^{18}F$ produced from cyclotron is flowed to scavenge. Saline solution is flowed to yield elute of metal-$^{18}F$ labeled compound, and the liquid is added with reaction solvent for dilution and passed through the Alumina N cartridge to give the complex.

Furthermore, the present invention provides a radiopharmaceutical product comprising the complex of the triazanonane derivatives and metal and fluorine as an effective component.

The complex is advantageously used as a radiopharmaceutical product using PET, or the like, due to stable octahedral structure with six ligands of the triazanonane derivatives and metal and F-18 which can label F-18 up to 78~90%.

Furthermore, the present invention provides a kit to form complex of the triazanonane derivatives and metal such as aluminum and fluorine-18. To be specific, the kit may be a F-18 labeling radioactive pharmaceutical product kit in apyrogenic sterilized form, in which liquid state of triazanonane derivatives and appropriate buffer solution is added in advance to facilitate F-18 labeling using metal chelating compound to the triazanonane derivatives, and which is distributed in a pharmaceutically-preferred sterilized vial and sealed for use, or for cooling, freezing or freeze-drying for later use.

EXAMPLES

The present invention will be elucidated below with reference to certain Examples and Experimental Examples. However, the Examples are given only for illustrative purpose and not to limit the concept of the present invention.

Example 1

Preparation of 4,7-bis(carboxymethyl)-1,4,7-triazonane-1-butyric acid

Step 1: Preparation of 4,7-bis(tert-butoxycarbonylmethyl)-1,4,7-triazonane-1-butyric acid ethyl ester

To the mixture liquid of NO2AtBu (0.05 g, 0.139 mmol) and K$_2$CO$_3$ (0.039 g, 0.279 mmol) in acetonitrile (2 mL), ethyl-4-bromobutyrate (0.030 g, 0.153 mmol) in acetonitrile (1 mL) liquid was slowly added, followed by stirring at room temperature for 20 hr. After confirming completion of the reaction with TLC (methylene chloride:methanol=9:1), fil-tration was carried out and the filtrate was dried under reduced pressure. The reactant was separated and purified by flash column chromatography (methylene chloride/methanol), and the product, i.e., 4,7-bis(tert-butoxycarbonylmethyl)-1,4,7-triazonane-1-butyric acid ethyl ester was purified with 6% methanol.

$^1$H NMR (CDCl$_3$, 300 MHz, 25° C.): δ 1.26 (t, 3H, J=9 Hz, 6 Hz), 1.46 (s, 18H), 1.84 (qn, 2H), 2.35 (t, 2H, J=6 Hz), 2.66-2.62 (m, 2H), 3.0-2.71 (m, 12H), 3.33 (s, 4H), 4.12 (q, 2H).

$^{13}$C NMR (CDCl$_3$, 75 MHz, 25° C.): δ 14.2, 28.2, 31.9, 51.5, 54.8, 55.1, 59.7, 60.3, 80.8, 171.4 (CO), 173.5 (CO) ppm.

ESI-MS: m/z=472.5 for [M+H]$^+$.

Step 2: Preparation of 4,7-bis(carboxymethyl)-1,4,7-triazonane-1-butyric acid

The ethanol liquid (0.5 mL) of the 4,7-bis(tert-butoxycarbonylmethyl)-1,4,7-triazonane-1-butyric acid ethyl ester (0.025 g, 0.0529 mmol) prepared at Step 1 was added with LiOH (0.0038 g, 0.159 mmol), followed by reaction at 50° C. for 24 hr. After confirming completion of the hydrolysis with ESI-mass, the reacted mixture was filtered through the Whatman syringe filter (0.45 μm) and dried under reduced pressure. The product was separated with RP-HPLC (10 mM HCl/EtOH; concentration increase from 0 to 40% for 20 min), and the filtrate underwent lyophilization to give final product.

$^1$H NMR (D$_2$O, 300 MHz, 25° C.): δ 1.45 (qn, 2H), 1.88 (t, 2H, J=4 Hz, 6 Hz), 2.80-2.40 (m, 14H), 3.25 (s, 4H).

$^{13}$C NMR (D$_2$O, 75 MHz, 25° C.): δ 23.9, 36.1, 52.1, 52.4, 53.1, 58.1, 62.0, 182.2 (CO), 183.7 (CO) ppm.

ESI-MS: m/z=332.2 for [M+H]$^+$.

Example 2

Preparation of 4,7-bis(carboxymethyl)-1,4,7-triazonane-1-pentanoic acid

Step 1: Preparation of 4,7-bis(tert-butoxycarbonylmethyl)-1,4,7-triazonane-1-pentanoic acid ethyl ester

The acetonitrile (2 mL) mixture liquid of NO2AtBu (0.05 g, 0.139 mmol) and K₂CO₃ (0.039 g, 0.279 mmol) was slowly added with acetonitrile (1 mL) liquid of ethyl-4-bromovalerate (0.030 g, 0.153 mmol), followed by stirring at room temperature for 20 hr. After confirming completion of the reaction with the TLC (methylene chloride:methanol=9:1), filtration was conducted and the filtrate was dried under reduced pressure. The reactant was separated and purified through the flash column chromatography (methylene chloride/methanol), and the product, i.e., 4,7-bis(tert-butoxycarbonyl methyl)-1,4,7-triazonane-1-pentanoic acid ethyl ester was purified with 5% methanol.

$^1$H NMR (CDCl₃, 300 MHz, 25° C.): δ 1.19 (t, 3H, J=6 Hz), 1.38 (s, 18H), 1.69-1.59 (m, 2H), 1.83-1.76 (m, 2H), 2.31 (t, 2H, J=6 Hz), 2.71-2.66 (m, 2H), 3.80-3.03 (m, 16H), 4.06 (q, 2H).

$^{13}$C NMR (CDCl₃, 75 MHz, 25° C.): δ 14.1, 21.8, 23.9, 28.1, 33.3, 48.8, 52.1, 55.5, 57.6, 60.4, 81.6, 170.6 (CO), 172.8 (CO) ppm.

ESI-MS: m/z=486.5 for [M+H]⁺.

Step 2: Preparation of 4,7-bis(carboxymethyl)-1,4,7-triazonane-1-pentanoic acid The ethanol (0.6 mL) liquid of the 4,7-bis(tert-butoxycarbonyl methyl)-1,4,7-triazonane-1-pentanoic acid ethyl ester (0.036 g, 0.0741 mmol) prepared at Step 1 was added with LiOH (0.0053 g, 0.222 mmol), and allowed to react at 50° C. for 24 hr. After confirming the conclusion of the hydrolysis reaction with the ESI-MASS, the reaction mixture was filtered through the Whatman syringe filter (0.45 μm) and dried under reduced pressure. The product was separated with RP-HPLC (10 mM HCl/EtOH; concentration increase from 0 to 40% for 20 min), and the filtrate underwent lyophilization to give final product.

$^1$H NMR (D₂O, 300 MHz, 25° C.): δ 1.51-1.35 (m, 4H), 2.08 (t, 2H, J=4 Hz), 2.85-2.35 (m, 12H), 3.16 (s, 4H).

$^{13}$C NMR (D₂O, 75 MHz, 25° C.): δ 17.4, 18.6, 24.3, 37.9, 52.0, 53.2, 58.1, 168.1 (CO), 181.7 (CO), 184.2 (CO) ppm.

ESI-MS: m/z=346.2 for [M+H]⁺.

Example 3

Preparation of 1-(2-amino-butyl)-4,7-bis(carboxymethyl)-1,4,7-triazanonane

Step 1: Preparation of NO2A'Bu-N-Boc-Alkylamine n = 4;

The acetonitrile (30 vol) mixture liquid of NO2A'Bu (1.5 eq) and K$_2$CO$_3$ (1.5 eq) was slowly added with acetonitrile (5 vol) liquid of N-protected alkylbromoamine (1.1 eq), followed by stirring at room temperature for 20 hr. After confirming completion of the reaction with TLC (methylene chloride:methanol=9:1), filtration was conducted, and the filtrate was dried under reduced pressure. The reactant was separated and purified with the flash column chromatography (methylene chloride/methanol), and the product, i.e., NO2A'Bu-N-Boc-alkylamine was purified with 5 and 10% methanol. The yield was 55-75%.

$^1$H NMR (CDCl$_3$, 300 MHz, 25° C.): δ 128-123 (m, 2H), 1.44 (s, 9H), 1.46 (s, 18H), 1.63-1.48 (m, 2H), 2.61-2.50 (m, 2H), 2.92-2.76 (m, 12H), 3.17-3.08 (m, 2H), 3.32 (s, 4H).

$^{13}$C NMR (CDCl$_3$, 75 MHz, 25° C.): δ 28.2, 28.4, 40.3, 50.7, 55.3, 55.5, 57.7, 59.8, 78.7, 80.7, 156.1 (CO), 171.5 (CO) ppm.

ESI-MS: m/z=529.4 for [M+H]$^+$.

Step 2: Preparation of 1-(2-amino-butyl)-4,7-bis(carboxymethyl)-1,4,7-triazanonane n = 2,3, and 4 n = 2,3, and 4

The 1,4-dioxane (30 vol) liquid of NO2A'Bu-N-Boc-alkylamine obtained at Step 1 was added with strong hydrochloric acid (5 vol), followed by stirring at room temperature. After confirming completion of the hydrolysis reaction with ESI-MASS, the reaction mixture was dried under reduced pressure, and repeatedly extracted with 1,4-dioxane and diethyl ether to give lightly yellow solid as the final product.

$^1$H NMR (D$_2$O, 300 MHz, 25° C.): δ 1.60-1.50 (m, 2H), 1.75-1.69 (m, 2H), 2.87-2.79 (m, 2H), 3.14 (s, 4H), 3.26-3.20 (m, 2H), 3.55-3.40 (m, 12H).

$^{13}$C NMR (D$_2$O, 75 MHz, 25° C.): δ 21.5, 24.3, 39.2, 50.1, 51.1, 51.4, 57.4, 57.7, 63.0, 173.3 (CO) ppm.

ESI-MS: m/z=316.2 for [M+H]$^+$.

Example 4

Preparation of cRGDyK-1,4,7-triazacyclononane-1,4-diacetate-7-butyramide

Step 1: Preparation of Bromine Derivative of Protected c(RGDyK)

15

-continued

4-bromobutyryl chloride (11.3 mg, 0.061 mmol) was added to the chloroform (2 mL) liquid of protected cRGDyK (50 mg, 51 μM) and triethylamine (20.6 mg, 0.204 mM) at 10° C. at which stirring was conducted for 7 hr. The completion of the reaction was confirmed with ESI mass spectrometry. The reacted mixture after the reaction was washed with water (5×2 mL), and the organic layer was evaporated. The remaining product was washed several times with diethyl ether to obtain a targeted product, i.e., the brom derivative of protected c(RGDyK) which was white solid.

ESI-MS: m/z=1132.2 for [M+H]$^+$ and 1052 for [M-Br]$^+$

16

Step 2: Preparation of Protected c(RGDyK)-NO2AtBu Complex)

The N,N-dimethylformamide (DMF) liquid of NO2AtBu (9.4 mg, 26.5 μM) and N,N-diisopropylethylamine (13.68 mg, 26.5 μM) was added with the brome derivatives (30 mg, 26.5 μM) of protected c(RGDyK) prepared at Step 1, followed by stirring at room temperature for 15 hr, and the completion of the reaction was confirmed with ESI⁺ mass spectrometry. The solvent was eliminated with rotary evaporator, and the remaining product was separated with RP-HPLC (Water-diluted 0.05% TFA (A)/ethanol (B); after flowing 30 and 100% ethanol for 30 min, liquid with a predetermined concentration gradient was flowed for 10 min). The peaks appearing retention time 26 min were recovered, and the final product was confirmed with mass spectrum. The solvent was evaporated, and the white solid of protected c(RGDyK)-NO2AtBu complex was obtained as a targeted compound.

ESI-MS: m/z=1409.7 for [M+H]⁺.

Step 3: Preparation of cRGDyK-1,4,7-triazacyclononane-1,4-diacetate-7-butyramide

The methylene chloride (3 mL) liquid of the protected c(RGDyK)-NO2AtBu complex (20 mg, 14.19 μM) obtained at Step 2 was slowly added with trifluoroacetic acid (TFA) at room temperature with stirring at room temperature. After stirring at room temperature for 20 hr, the solvent was evaporated. The final product was separated and purified by RP-HPLC (30 and 100% ethanol for 30 min).

ESI-MS: m/z=688.4 for [M+H]⁺.

Example 5

Preparation of 4,7-bis(carboxymethyl)-1-(4-aminobenzyl)-1,4,7-triazanonane

Step 1: Preparation of 4,7-bis(tert-butoxycarbonylmethyl)-1-(4-nitrobenzyl)-1,4,7-triazanonane The anhydrous acetonitrile (2 mL) liquid of NO2A-tBu (0.05 g, 0.139 mmol) and $K_2CO_3$ (0.025 g, 0.139 mmol) was slowly added with acetonitrile (0.5 mL) liquid of 4-nitrobenzylbromide (0.03 g, 0.139 mmol), followed by stirring at room temperature for 20 hr. The completion of the reaction was confirmed through TLC ($CH_2Cl_2$/MeOH=9:1, v/v). The reaction mixture was filtered, and the solvent was dried under reduced pressure, separated and purified by column chromatography ($CH_2Cl_2$/MeOH), and the final product was obtained under eluant of 7% MeOH.

ESI-MS: m/z=493.3 for $[M+H]^+$.

Step 2: Preparation of 4,7-bis(carboxymethyl)-1-(4-nitrobenzyl)-1,4,7-triazanonane 4,7-bis(tert-butoxycarbonyl methyl)-1-(4-nitrobenzyl)-1,4,7-triazanonane (0.02 g, 0.0407 mmol) obtained at Step 1 was dissolved in 4 M HCl of 1,4-dioxane (3 mL) liquid, followed by stirring at room temperature for 24 hr. The completion of the reaction was confirmed with ESI mass spectrometry, the solvent was dried under reduced pressure, and the final product was obtained in the form of hydrochloride.

ESI-MS: m/z=381.2 for $[M+H]^+$.

Step 3: Preparation of 4,7-bis(carboxymethyl)-1-(4-aminobenzyl)-1,4,7-triazanonane 4,7-bis(carboxymethyl)-1-(4-nitrobenzyl)-1,4,7-triazanonane (0.01 g, 0.026 mmol) obtained at Step 2 was dissolved in 2 mM KOH of MeOH (2 mL) liquid, followed by addition of palladium-carbon (Pd—C, 10%) under nitrogen condition. The reaction mixture was reacted under hydrogen gas for 8 hr. After the reaction mixture was filtered with celite, the solvent was evaporated, followed by dissolution in water for separation and purification with RP-HPLC (100% 0.05% TFA for 5 min, 0 to 80% EtOH for another 25 min). The peaks appearing at 15 min were recovered, and the white solid as the final product was obtained after drying.

ESI-MS: m/z=351.2 for $[M+H]^+$.

Example 6

Preparation of 4,7-bis(carboxymethyl)-1-(4-isothiocyanatobenzyl)-1,4,7-triazanonane

Comparative Example 2

Preparation of 4,7-bis(tert-butoxycarbonylmethyl)-1,4,7-triazonanane-1-propionic acid Step 1: Preparation of 4,7-bis(tert-butoxycarbonylmethyl)-1,4,7-triazonane-1-propionic acid 4,7-bis(carboxymethyl)-1-(4-aminobenzyl)-1,4,7-triazanonane (0.006 g, 0.017 mmol) obtained at Example 6 and CaCO$_3$ (0.002 g, 0.026 mmol) were dissolved in water (1 mL) and chloroform (1 mL), followed by dropwise addition of thiophosgene (0.01 mL) and stirring overnight. After stirring, the reaction mixture was filtered, and the solvent was dried under reduced pressure, followed by separation and purification with RP-HPLC (100% TFA for 5 min, 0 to 100% B for another 25 min). The peaks appearing at 24 min were recovered and the final product was obtained.

ESI-MS: m/z=393.3 for [M+H]$^+$.

Comparative Example 1

NOTA

NOTA was purchased from Sigma-Aldrich Corporation.

The acetonitrile (2 mL) mixture liquid of NO2AtBu (0.05 g, 0.139 mmol) and Et$_3$N (0.028 g, 0.279 mmol) was slowly added with acetonitrile (1 mL) liquid of 3-bromopropionic acid (0.021 g, 0.14 mmol), followed by stirring at room temperature for 36 hr. After confirming completion of the reaction with TLC (methylene chloride:methanol=9:1), the filtrate was dried under reduced pressure. The reactant was dissolved in methylene chloride (5 mL) and washed with water (3 mL) and brine (3 mL). The organic layer was dried under reduced pressure, followed by separation and purification with flash column chromatography (methylene chloride/methanol) to give 4,7-bis(tert-butoxycarbonyl methyl)-1,4,7-triazonane-1-propionic acid which was purified with 8% methanol.

$^1$H NMR (CDCl$_3$, 300 MHz, 25° C.): δ 1.34-125 (m, 2H), 1.44 (s, 18H), 2.64 (t, 2H, J=6 Hz), 2.76 (s, 4H), 3.16-3.04 (m, 4H), 3.46-3.30 (m, 8H), $^{13}$C NMR (CDCl$_3$, 75 MHz, 25° C.): δ 8.6, 28.1, 45.3, 51.4, 52.9, 54.0, 57.8, 81.3, 171.0 (CO), 1742 (CO) ppm.

ESI-MS: m/z=430.5 for [M+H]$^+$.

Step 2: Preparation of 4,7-bis(tert-butoxycarbonylmethyl)-1,4,7-triazonanane-1-propionic acid The 1,4-dioxane (2 mL) liquid of 4,7-bis(tert-butoxycarbonyl methyl)-1,4,7-triazonane-1-propionic acid (0.015 g, 0.0349 mmol) was added with strong hydrochloric acid (0.2 mL), and allowed to react at 50° C. for 24 hr. After confirming completion of the hydrolysis with ESI-MASS, the reaction mixture was filtered through the Whatman syringe filter (0.45 μm), followed by drying under reduced pressure. The product was repeatedly extracted with 1,4-dioxane and diethyl ether to give lightly yellow solid.

$^1$H NMR (D$_2$O, 300 MHz, 25° C.): δ 2.79 (t, 2H, J=6 Hz), 3.15-3.110 (m, 4H), 3.35-3.22 (m, 4H), 3.52-3.45 (m, 4H), 3.54 (s, 4H), 3.75-3.72 (m, 2H).

$^{13}$C NMR (D$_2$O, 75 MHz, 25° C.): δ 29.3, 50.0, 51.0, 51.8, 53.8, 57.4, 63.0, 173.3 (CO), 174.5 (CO) ppm.

ESI-MS: m/z=318.2 for [M+H]$^+$.

Comparative Example 3

Preparation of 1-(2-amino-ethyl)-4,7-bis(carboxymethyl)-1,4,7-triazonanonane

The target compound, i.e., 1-(2-amino-ethyl)-4,7-bis(carboxymethyl)-1,4,7-triazonanonane was obtained in the same manner as Example 4, except for difference that ethylbromoamine was used instead of butylbromoamine.

$^1$H NMR (D$_2$O, 300 MHz, 25° C.): δ 3.18-2.86 (m, 14H), 3.52-3.43 (m, 2H), 3.69 (s, 4H).

$^{13}$C NMR (D$_2$O, 75 MHz, 25° C.): δ 36.2, 49.8, 50.5, 51.3, 53.6, 56.8, 60.8, 172.8 (CO) ppm.

ESI-MS: m/z=289.3 for [M+H]$^+$.

Comparative Example 4

Preparation of 1-(2-amino-propyl)-4,7-bis(carboxymethyl)-1,4,7-triazonanonane

Except for difference that propylbromoamine was used instead of butylbromoamine, target compound, i.e., 1-(2-amino-propyl)-4,7-bis(carboxymethyl)-1,4,7-triazonanonane was obtained in the same manner as Example 4.

$^1$H NMR (D$_2$O, 300 MHz, 25° C.): δ 2.19-1.98 (m, 2H), 2.90 (t, 2H, J=4 Hz), 3.11 (s, 4H), 3.35-3.21 (m, 4H), 3.52-3.41 (m, 6H), 3.71 (s, 4H).

$^{13}$C NMR (D$_2$O, 75 MHz, 25° C.): δ 22.7, 37.0, 49.9, 51.1, 51.6, 55.0, 57.3, 173.5 (CO) ppm.

ESI-MS: m/z=303.2 for [M+H]$^+$.

Comparative Example 5

Preparation of 4,7-bis(carboxymethyl)-1,4,7-triazononane-1-oxo-butyric acid

Step 1: Preparation of 4,7-bis(tert-butoxycarbonylmethyl)-1,4,7-triazonane-1-oxo-butyric acid

The chloroform (3 mL) mixture liquid of NO2AtBu (0.1 g, 0.278 mmol) and Et$_3$N (0.034 g, 0.336 mmol) was slowly added with chloroform (1 mL) liquid of succinic anhydride (0.031 g, 0.336 mmol), followed by stirring at room temperature for 24 hr. The completion of the reaction was confirmed with TLC (methylene 7-chloride:methanol=9:1). The reaction mixture was washed with water (2 mL) and brine (2 mL). The organic layer was dried under reduced pressure, followed by separation and purification with flash column chromatography (methylene chloride/methanol), to give 70 mg of 4,7-bis(tert-butoxycarbonyl methyl)-1,4,7-triazonane-1-oxo-butyric acid.

$^1$H NMR (CDCl$_3$, 300 MHz, 25° C.): δ 1.46 (s, 18H), 2.70-2.66 (m, 2H), 3.21-2.82 (m, 8H), 3.27-3.22 (m, 2H), 3.47 (s, 4H), 3.70-3.59 (m, 4H).

$^{13}$C NMR (CDCl$_3$, 75 MHz, 25° C.): δ 28.0, 28.7, 30.0, 45.0, 50.4, 50.7, 58.2, 58.7, 81.7, 171.0 (CO), 173.5 (CO) ppm.

ESI-MS: m/z=458.2 for [M+H]$^+$.

Step 2: Preparation of 4,7-bis(carboxymethyl)-1,4,7-triazononane-1-oxo-butyric acid The 1,4-dioxane (3 mL) liquid of 4,7-bis(tert-butoxycarbonyl methyl)-1,4,7-triazonane-1-oxo-butyric acid (0.007 g) obtained at Step 1 was added with strong hydrochloric acid (0.3 mL) and allowed to react at room temperature. After confirming the completion of the hydrolysis reaction with ESI-MASS, the reaction mixture was dried under reduced pressure. The repetitive extraction with 1,4-dioxane and diethyl ether gave 22 mg of lightly yellow solid as the final product.

$^1$H NMR (D$_2$O, 300 MHz, 25° C.): δ 2.53-2.41 (m, 2H), 2.99-2.82 (m, 4H), 3.22-3.14 (m, 2H), 3.48-3.30 (m, 4H), 3.52 (s, 4H), 3.61-3.53 (m, 4H).

$^{13}$C NMR (D$_2$O, 75 MHz, 25° C.): δ 29.1, 29.5, 46.4, 47.2, 54.0, 55.2, 56.1, 170.2 (CO), 175.3 (CO), 176.7 (CO) ppm.

ESI-MS: m/z=346.2 for [M+H]$^+$.

Experimental Example 1

F-18 Labeling

The compounds synthesized according to the Examples and Comparative Examples were labeled with $^{18}$F and the labeling efficiency was analyzed. Dissolving AlCl$_3$.6H$_2$O in 0.1M sodium acetate buffer solution (pH 4) gave 2 mM AlCl$_3$ stock liquid. After activation under stream of 0.4 M KHCO$_3$ (5 mL) and distilled water (10 mL) on QMA light cartridge, $^{18}$F produced from cyclotron was flowed to scavenge. Saline solution (0.4 mL) was flowed to the cartridge to elute $^{18}$F, to which AlCl$_3$ stock liquid was added and left at room temperature for 10 min to give Al$^{18}$F liquid containing 27~90 mmol of Al. The compounds of Examples and Comparative Examples (each 30~100 nM) were dissolved in 0.1 M of sodium acetate buffer solution (1 mL), and Al$^{18}$F liquid prepared as explained above was added, followed by reaction for 10 min in the heating block heated to 110° C. for labeling. The saline solution (0.4 mL) was flowed to the cartridge, giving 27~90 mmol Al$^{18}$F. labeled compound which was passed through the Alumina N cartridge for purification. The labeling efficiency was calculated by detecting radioactive distribution with TLC scanner (Bioscan AR-2000) and autoradiography (BAS2500 Imaging System), following developing to 75% MeCN with Instant Thin Layer Chromatography Silica Gel (ITLC-SG, Gelman Science, Ann Arbor, Mich.).

Figure 1:
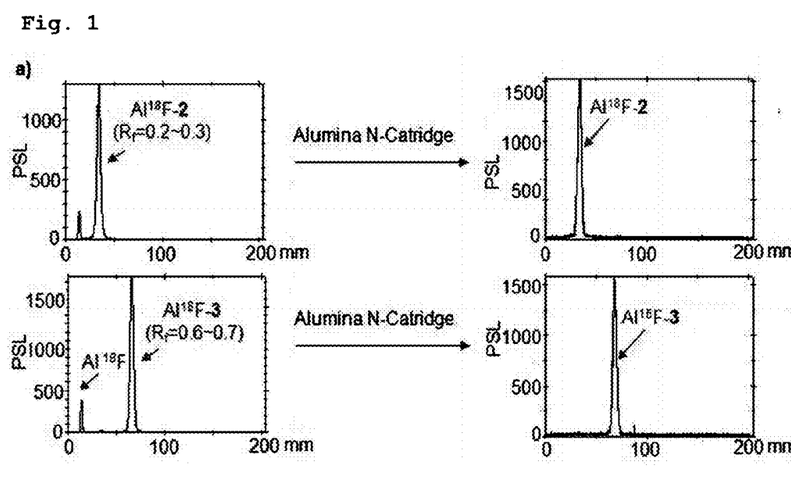
FIG. 1 is an autoradiographic image of non-labeled $^{18}$F distills according to an embodiment of the present invention.
Figure 2:
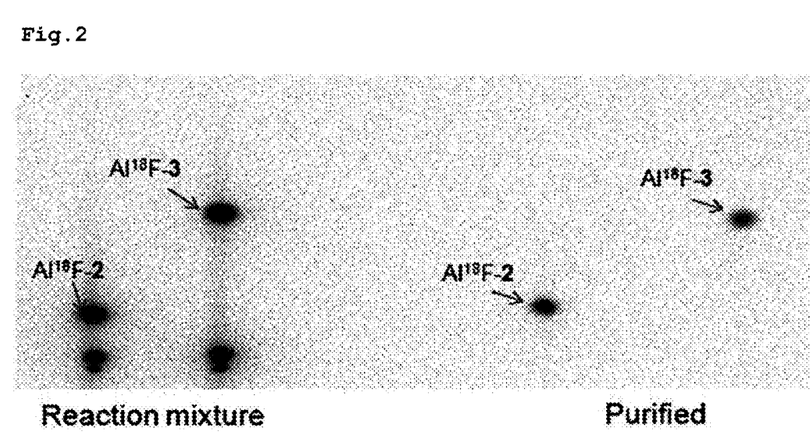
FIG. 2 is a TLC scanner image of non-labeled $^{18}$F distills according to an embodiment of the present invention.

The ITLC after labeling confirmed that non-labeled $^{18}$F remained at original spots, while the labeled compounds had Rf present between 0.2~0.7 based on TLC scanner and autoradiography, and FIGS. 1 and 2 also confirm that the non-labeled $^{18}$F was completely removed by filtering through the alumina N cartridge and purification.

The labeling efficiency of the respective compounds were obtained and listed as below.

TABLE 2

$^{18}$F labeling efficiency of NO2A derivatives

| Compound | Labeling efficiency(%) |
| --- | --- |
| NOTA | 10.9 |
| NO2A | 89.3 |
| NO2A-Bz | 83.0 |
| Comp. Ex. 2 Compound | 23.6 |
| Comp. Ex. 5 Compound | 32.9 |
| Example 1 Compound | 86.1 |
| Example 2 Compound | 77.8 |

Table 2 indicates that the labeling efficiency was lowest in the order of NOTA and Comp. Ex. 2 Compound. On the contrary, NO2A exhibited the highest labeling efficiency, and Example 1 compound and Example 2 compound exhibited high labeling efficiency. In NOTA or Comparative Example 2 compound, two carboxyl groups first bond to Al—$^{18}$F, leaving possibility that one remaining carboxyl group bonds to Al, forming pentagonal or hexagonal structure which is relatively stable. Accordingly, since bonding between Al and $^{18}$F is hindered, the labeling efficiency decreases. On the contrary, in Example 1 compound or Example 2 compound, bonding to Al forms heptagonal or octagonal structure which is relatively unstable. Accordingly, as bonding with $^{18}$F weakens, $^{18}$F more readily bonds to Al, and the labeling efficiency increases. The above indicates that it is more advantageous for the purpose of $^{18}$F labeling when the electron-doner such as oxygen, nitrogen, sulfur or phosphor that can complete with $^{18}$F is away from the site where this can bond to Al in pentagonal or hexagonal structure. Based on this, NO2A and NO2A-Bz compounds exhibited very good labeling efficiency. Further, Comparative Example 5 compound, which has oxygen atom at a site that forms heptagonal structure, exhibited deteriorated labeling efficiency due to influence of carbonyl group, which is attached to the nitrogen of the ring, to the ring structure.

Experimental Example 2

AlF-NO2A-Bz Synthesis and X-Ray Crystallographic Structure

The aqueous solution of NO2A-Bz, i.e., 1-benzyl-4,7-bis (carboxymethyl)-1,4,7-triazonane (0.07 g, 0.1886 M) and AlCl$_3$ (0.029 g, 0.226 mM) was added with 1 M of sodium acetate buffer solution to adjust pH to 3.5. After heating the compound in boiling water tank, NaF (0.039 g, 0.943 mM) was added, followed by additional heating for 30 min. The formation of complex was confirmed with ESI-MASS. After the reaction completed, RP-HPLC separation (water/EtOH; variation at EtOH concentration of 0 to 70% for 30 min) was conducted (Rt=15 min). The collected fractions underwent lyophilization to give white, crumbly solid which was dissolved in water/EtOH (2:8) and slowly evaporated to give crystal.

ESI-MS: m/z=380.1 for [M+H]$^+$, 402.2 for [M+Na]$^+$.

The crystal structure was analyzed by the laboratory of organic metals, Seoul National University. The single crystal diffraction data was measured using Enraf-Nonius CCD single-crystal X-ray diffractometer, at room temperature using graphite-monochromated. MoKα radiation (λ=0.71073 Å). First, the position matrix and unit cell parameters were obtained from the first 10 frames, and the entire data was precision calibrated with the angle set at 3°<θ<27°. About 7,500 times of reflection were collected in total, and more than half of these exhibited characteristic values. The frames were combined, and Lorentz and polarization effect were calibrated using DENZO to give the crystal structure as illustrated in FIG. 3.

Referring to FIG. 3, the octahedral structure with six ligands was formed, in which three N atoms and two carboxyl groups of the triazanonane ring bonded to aluminum, and fluorine was also attached to aluminum. Accordingly, it was confirmed that the complex of the derivatives, metal and fluorine according to the present invention forms octahedral structure which maintains stable state and thus increases fluorine labeling efficiency.

Experimental Example 3

Stability Test

Figure 4:
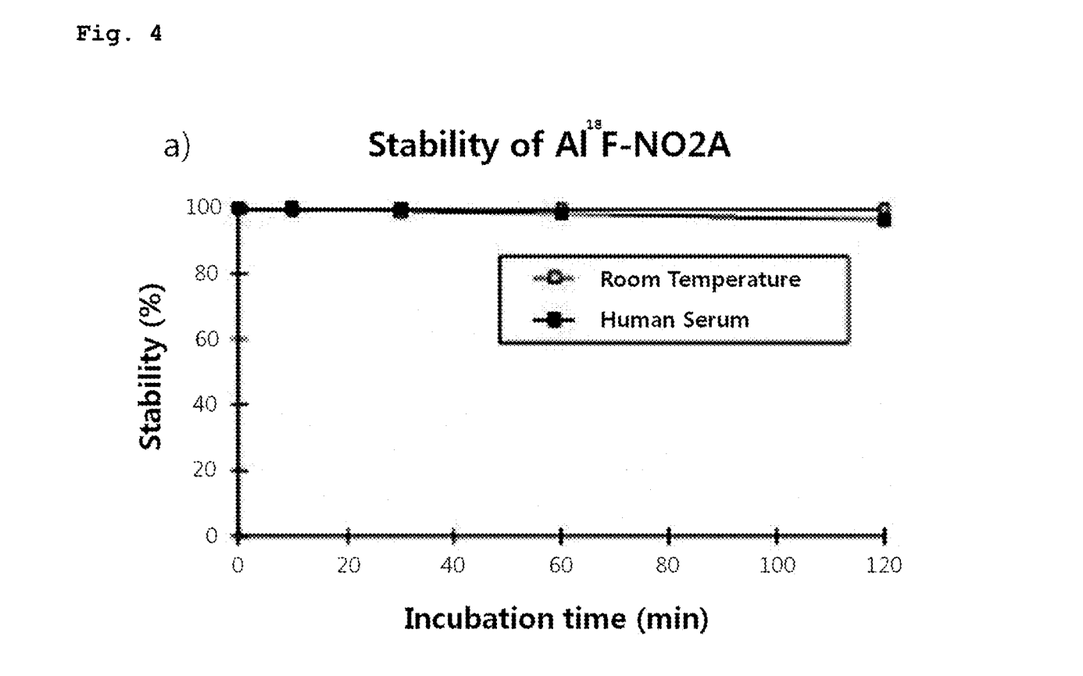
FIG. 4 an is ITLC image, illustrating stability after $^{18}$F—Al labeling in NO2A according to an embodiment of the present invention.
Figure 5:
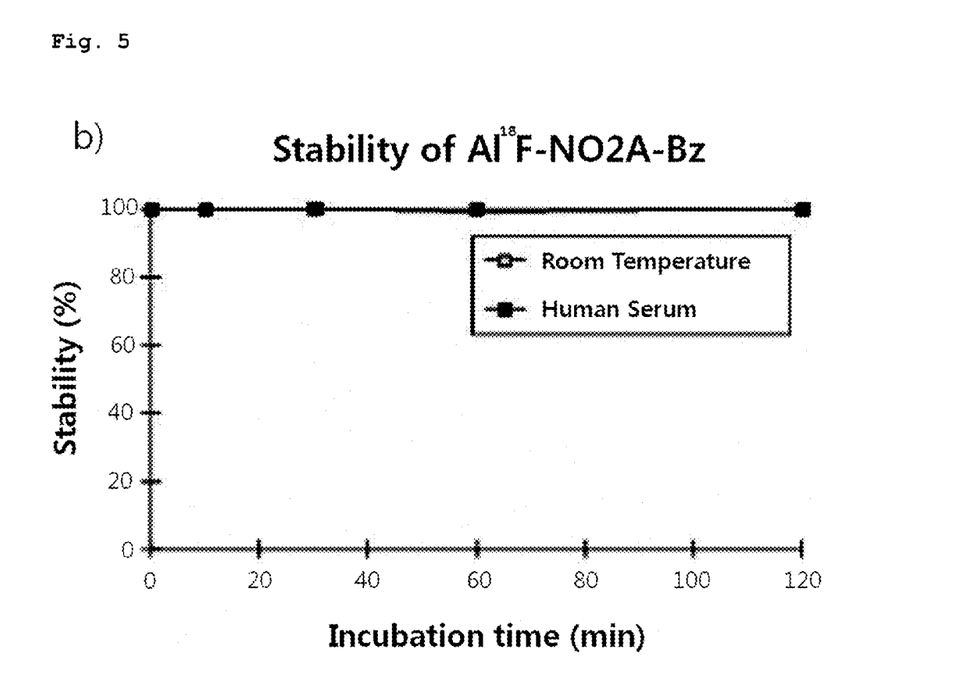
FIG. 5 is an ITLC image, illustrating stability after $^{18}$F—Al labeling in NO2A-benzyl according to an embodiment of the present invention.
Figure 6:
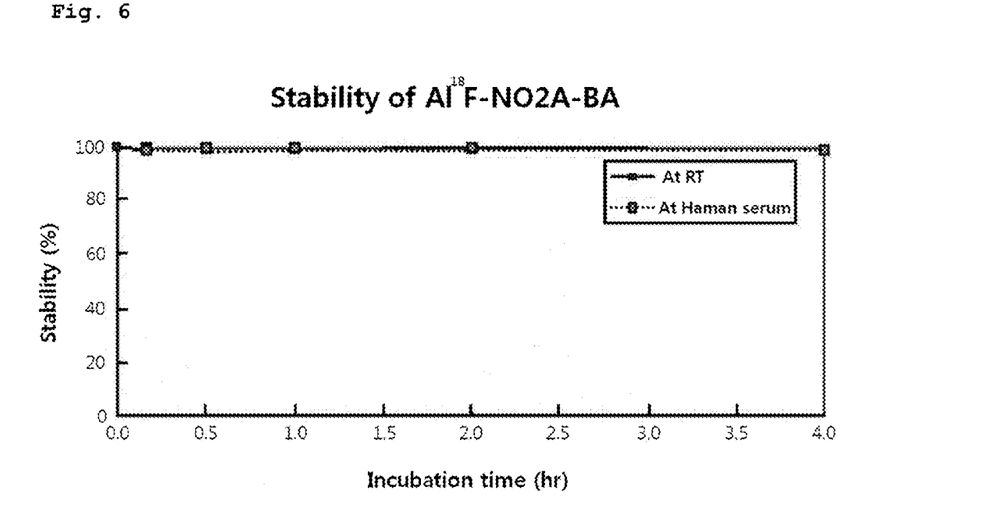
FIG. 6 is an ITLC image, illustrating stability after $^{18}$F—Al labeling in NO2A-butyric acid according to an embodiment of the present invention

To investigate room temperature stability and stability in 37° C. human serum, the labeling compounds were cultured for 10 min, 30 min, 60 min, and 120 min under the conditions explained above, and the degree of decomposition of the compounds with ITLC, by spreading with 70% acetonitrile were obtained as illustrated in FIGS. 4, 5 and 6. The result confirmed good stability for 2 hr.

Experimental Example 4

Human Serum Protein Binding Measurement

The labeling compounds were cultured in human serum (1 mL) at 37° C. for 10 min and 60 min, and loaded to PD-10 column (pre-conditioned with 1 mL of 1% BSA/0.1 M DTPA), swept under stream of PBS into 30 test tubes by 0.5 mL fractions each. The radioactivity of each test tube was measured with gamma counter, and 2 L of sample was collected from the respective test tubes. After impression on the paper filter and staining with Coomassie blue, the protein peaks were observed. By plotting a curve of radioactivity of the respective fractions and calculating protein binding percent, the result was obtained as shown in Table 3.

TABLE 3

| Human serum protein binding percent | |
|---|---|
| Compound | Protein binding (%) |
| $^{68}$Ga—NO2A | 0.23 ± 0.06 |
| $^{68}$Ga—NO2A-Bz | 0.06 ± 0.01 |
| $^{68}$Ga—NO2A-BA (Example 1) | 0.79 ± 0.12 |

Referring to Table 3, it was confirmed that the compound of Example 1 exhibited three times higher binding to human serum protein than NO2A compound.

The foregoing exemplary embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims.

The invention claimed is:

1. A triazanonane derivative depicted in Chemical Formula 1 or pharmaceutically acceptable salt thereof:

[Chemical Formula 1]

where R$^1$ and R$^2$ are independently OH, SH, NH$_2$ or C$_1$~C$_{10}$ alkoxy;
A is CH$_2$, C(=S) or C(=O);
E is CH$_2$, C(=S), C(=O) or phenyl;
X is atom group with biological activity or linker activated or activatable to bond to another molecule;
n is an integer between 0 and 10 when E is phenyl,
n is an integer between 3 and 10 when E is CH$_2$, C(=S) or C(=O); and
m is an integer between 0 and 5.

2. The triazanonane derivative expressed by Chemical Formula 1 or pharmaceutically acceptable salt thereof according to claim 1, wherein
each of R$^1$ and R$^2$ is independently OH or t-butoxy;
A is CH$_2$ or C(=O);
E is CH$_2$, C(=O) or phenyl;
X is atom group selected from amino acid, peptide, protein, nucleic acid, vitamin, hormone, neurotransmitter, sugar, nanoparticle, microparticle, fat, fatty acid, nitroimidazole or derivatives thereof;
n is an integer between 0 and 10 when E is phenyl, n is an integer between 3 and 10 when E is CH$_2$ or C(=O); and
m is an integer between 0 and 3.

3. The triazanonane derivative expressed by Chemical Formula 1 or pharmaceutically acceptable salt thereof according to in claim 1, wherein
X is selected from the group consisting of carboxyl, hydroxyl, amine, halogen, N-hydroxysuccinimide ester, tetrafluorophenol ester, pentafluorophenol ester, maleimide, haloacetate, hydrazine, hydroxylamine, sulfhydryl, thioester, desulfide, aldehyde, isothiocyanate azide and acetylene.

4. The triazanonane derivative expressed by Chemical Formula 1 or pharmaceutically acceptable salt thereof according to claim 2, wherein
X is selected from the group consisting of octreotide derivatives, bombesin, vasoactive intestinal peptide (VIP), cholecystokinin, neurotensin, EGF, VEGF, RGD, CXCR4 ligand, substance P, matrix metalloproteinase (MMP), lysine glutamate urea, and cysteine glutamate urea.

5. The triazanonane derivative expressed by Chemical Formula 1 or pharmaceutically acceptable salt thereof according to claim 1, wherein the triazanonane derivative is selected from the group consisting of:
1) 4,7-bis(carboxymethyl)-1,4,7-triazonane-1-butyric acid;
2) 4,7-bis(carboxymethyl)-1,4,7-triazonane-1-pentanoic acid;
3) 1-(1-amino-butyl)-4,7-bis(carboxymethyl)-1,4,7-triazanonane;
4) cRGDyK-1,4,7-triazacyclononane-1,4-diacetate-7-butylamide;
5) 4,7-bis(carboxymethyl)-1-(4-aminobenzyl)-1,4,7-triazanonane; and
6) 4,7-bis(carboxymethyl)-1-(4-isothiocyanatobenzyl)-1,4,7-triazanonane.

6. A complex comprising the triazanonane derivative according to claim 1 and metal and fluoride.

7. The complex according to claim 6, wherein the fluoride is F-18.

8. The complex according to claim 6, wherein the metal is aluminum, gallium, indium, thallium, yttrium or ruthenium.

9. The complex as set forth in claim 6, wherein the metal is aluminum.

10. A radiopharmaceutical product comprising the triazanonane derivative according to claim 1 and metal and F-18.

11. A kit comprising a complex of the triazanonane derivative according to claim 1 and metal and F-18.

\* \* \* \* \*

UNITED STATES PATENT AND TRADEMARK OFFICE
CERTIFICATE OF CORRECTION

PATENT NO. : 9,012,604 B2  
APPLICATION NO. : 13/983053  
DATED : April 21, 2015  
INVENTOR(S) : Jeong et al.

Page 1 of 1

It is certified that error appears in the above-identified patent and that said Letters Patent is hereby corrected as shown below:

ON THE TITLE PAGE:

Item (73) (Assignee): Replace "Snur & DB Foundation, Seoul (KR)" with -- "SNU R & DB Foundation, Seoul (KR)" --.

Signed and Sealed this  
Twenty-fifth Day of August, 2015

Michelle K. Lee  
*Director of the United States Patent and Trademark Office*